(12) United States Patent
Lee et al.

(10) Patent No.: US 9,238,839 B2
(45) Date of Patent: Jan. 19, 2016

(54) PRIMER SET, METHOD AND KIT FOR DETECTING PATHOGEN IN ANIMALS OR PLANTS

(71) Applicant: NATIONAL CHENG KUNG UNIVERSITY, Tainan (TW)

(72) Inventors: Gwo-Bin Lee, Tainan (TW); Wen-Hsin Chang, Tainan (TW); Chih-Hung Wang, Tainan (TW); Tzong-Yueh Chen, Tainan (TW); Ting-Yu Wang, Tainan (TW); Long-Huw Lee, Tainan (TW); Jia-Ling Yang, Tainan (TW); Hui-Liang Wang, Tainan (TW); I-Chin Wang, Tainan (TW); Chih-Chieh Chuang, Tainan (TW); Fuh-Jyh Jan, Tainan (TW); Ping-Chen Li, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 173 days.

(21) Appl. No.: 13/785,734

(22) Filed: Mar. 5, 2013

(65) Prior Publication Data
US 2014/0024014 A1 Jan. 23, 2014

(30) Foreign Application Priority Data
Jul. 23, 2012 (TW) .............................. 101126506 A

(51) Int. Cl.
*C12Q 1/68* (2006.01)
*C12Q 1/70* (2006.01)

(52) U.S. Cl.
CPC .............. *C12Q 1/6888* (2013.01); *C12Q 1/689* (2013.01); *C12Q 1/6895* (2013.01); *C12Q 1/70* (2013.01); *C12Q 1/701* (2013.01); *C12Q 2600/16* (2013.01)

(58) Field of Classification Search
None
See application file for complete search history.

(56) References Cited

U.S. PATENT DOCUMENTS

| 8,916,749 | B2 * | 12/2014 | Brugiere | ........................ 800/298 |
| 2000/5607835 | | 3/1997 | Reeves et al. | |
| 2006/0115820 | A1 | 6/2006 | Koizumi et al. | |

FOREIGN PATENT DOCUMENTS

| IL | WO2007017759 | * | 2/2007 | ............. C12N 15/11 |
| TW | 201224152 | A1 | 6/2012 | |

OTHER PUBLICATIONS

Notomi et al. (Nucleic Acids Research, 2000, 28(12):e63, p. i-vii).*
Lin et al. (Biochem. Biophys. Res. Commun., 2006, 351 (2), 534-539).*
Fujino et al. (J Med Virol, 2005, 406-413).*
Dhar et al., "Quantitative assay for measuring the Taura syndrome virus and yellow head virus load in shrimp by real-time RT-PCR using SYBR Green chemistry", J. Virol. Methods, 2002, vol. 104, pp. 69-82.
Nishizawa et al., "Comparison of the coat protein genes of five fish nodaviruses, the causative agents of viral nervous necrosis in marine fish", J. Gen. Virol., 1995, vol. 76, pp. 1563-1569.
Dalla Valle et al., "Development of a sensitive and quantitative diagnostic assay for fish nervous necrosis virus based on two-target real-time PCR", Vet. Microbiol. 2005, vol. 110, pp. 167-179.
Grotmol et al., "Characterisation of the capsid protein gene from a nodavirus strain affecting the Atlantic halibut *Hippoglossus hippoglossus* and design of an optimal reverse-transcriptase polymerase chain reaction (RT-PCR) detection assay", Dis. Aquat. Organ. 2000, vol. 39, pp. 79-88.
Mori et al., "Detection of Loop-Mediated Isothermal Amplification Reaction by Turbidity Derived from Magnesium Pyrophosphate Formation", Biochem. Biophys. Res. Commun., 2001, vol. 289, pp. 150-154.
Tomita et al., "Loop-mediated isothermal amplification (LAMP) of gene sequences and simple visual detection of products", Nat. Protoc. 2008, vol. 3, No. 5, pp. 877-882.
Piepenburg et al., "DNA Detection Using Recombination Proteins", PLoS Biol., 2006, vol. 4, issue 7, pp. e204.
Starkey et al., "Detection of piscine nodaviruses by real-time nucleic acid sequence based amplification (NASBA)", Dis. Aquat. Organ., 2004, vol. 59, pp. 93-100.
Walker et al., "Multiplex strand displacement amplification (SDA) and detection of DNA sequences from Mycobacterium tuberculosis and other mycobacteria", Nucleic Acids Res., 1994, vol. 22, pp. 2670-2677.
Notomi et al, "Loop-mediated isothermal amplification of DNA", Nucleic Acids Res., 2000, vol. 28, No. 12, pp. e63.
Nagamine et al., "Accelerated reaction by loop-mediated isothermal amplification using loop primers", Mol. Cell. Probes, 2002, vol. 16, pp. 223-229.
Savan et al., "Sensitive and Rapid Detection of Edwardsiellosis in Fish by a Loop-Mediated Isothermal Amplification Method", Appl. Environ. Microbiol., 2004, vol. 70, pp. 621-624.
Gunimaladevi et al., "A loop mediated isothermal amplification (LAMP) method for detection of infectious hematopoietic necrosis virus (IHNV) in rainbow trout", Arch. Virol., 2005, vol. 150, pp. 899-909.
Yang et al., "A pneumatic micropump incorporated with a normally closed valve capable of generating a high pumping rate and a high back pressure", Microfluid. Nanofluid., 2009, vol. 6, pp. 823-833.
Hsieh et al., "A two-dimensional, self-compensated, microthermal cycler for one-step reverse transcription polymerase chain reaction applications", Microfluid. Nanofluid., 2009, vol. 6, pp. 797-809.

(Continued)

*Primary Examiner* — Stephanie K Mummert
(74) *Attorney, Agent, or Firm* — WPAT, P.C.; Anthony King

(57) ABSTRACT

The invention provides a method for rapidly detecting a pathogen in animals or plants comprising using a specific primer set and nucleic acid in a sample to carry on a loop-mediated isothermal amplification. If at least one amplification occurs, the sample comprises the pathogen. The invention also provides a primer set, probe and kit for detecting a pathogen in animals or plants.

12 Claims, 2 Drawing Sheets

(56) References Cited

OTHER PUBLICATIONS

Hawkins et al., "DNA purification and isolation using a solid-phase", Nucleic Acids Res., 1994, vol. 22, pp. 4543-4544.
Chang et al., 2012 7th IEEE International Conference on Nano/Micro Engineered and Molecular Systems, (Includes "An optical diagnostic system using isothermal amplification technique for Phalaenopsis orchids"), 2012.
Office Action issued on Jan. 28, 2014 to the corresponding ROC (Taiwan) Patent Application No. 101126506.
Foreign document listed above, 201224152 A1, corresponds to US2012141989A1 published Jun. 7, 2012.
Wataru Yamazaki et al., "Sensitive and rapid detection of cholera toxin-producing Vibrio cholerae using a loop-mediated isothermal amplification", BMC Microbiology 2008, 8:94, pp. 1-7.
Wataru Yamazaki et al., Development of a loop-mediated Isothermal amplification assay for sensitive and rapid detection of Vibrio parahaemolyticus, BMC Microbiology Sep. 2008, 8:163, pp. 1-7.
Siyi Chen et al., "Development of a toxR-base loop-mediated isothermal amplification assay for detecting Vibrio parahaemolyticus", BMC Microbiology 2010, 10:41.
Feifei Han et al., "Detecting Potentially Virulent Vibrio vulnificus Strains in Raw Oysters by Quantitative Loop-mediated Isothermal Amplification", Applied and Environmental Microbiology, Apr. 2011, p. 2589-2595.

\* cited by examiner

PRIMER SET, METHOD AND KIT FOR DETECTING PATHOGEN IN ANIMALS OR PLANTS

BACKGROUND OF THE INVENTION

1. Field of the Invention

The invention relates to an animal or plant pathogen detection, and more particularly, to an animal or plant pathogen detection using a loop-mediated isothermal amplification (LAMP) system.

2. Description of the Related Art

The detection of a nucleic acid fragment is widely used in various fields and important. For example, the rapid and accurate detection of a target nucleic acid fragment can be applied for quickly diagnosing a pathogen and is benefit for early prevention.

Agriculture once had a great contribution in the gross domestic product (GDP). However, with the social change and the improvement of the national income in recent years, the economic structure has been transformed mainly to the business and services. Agriculture is facing the internal industrial structure changes. The unstable world food supply, climate change, and high infection rate impact the agriculture industry. Reducing the infection rate is one of the object to improve the agricultural development.

Animal and plant health inspection and quarantine is an important procedure in the international exchanges in order to avoid or reduce the hazards of infectious diseases in animals, plants and products thereof, and further to safeguard the health of citizens. In 1997, Taiwan has undergone the foot-and-mouth disease, betting a total of fifteen billion in the epidemic prevention work and causing the economic losses of one hundred seventy billion. If the early diagnosis and early epidemic prevention works, the farmers' and the country's economic losses can be reduced. Therefore, in the international or domestic forward-looking development, research and study of the diagnosis and identification in the animal and plant health inspection and quarantine are the core objectives. Only with the assistance of the fast and sensitive diagnostic identification technology, the biological monitoring, checking, validation, prevention, and risk analysis and other quarantine can be effectively executed. As the reason, the diagnostic identification in the animal and plant health inspection and quarantine is the core area therein. However, the effective integration of the diagnosis and identification in the animal and plant health inspection and quarantine still lacks, and although the point of breakthrough occurs, it is difficult to have a comprehensive development.

With the development of the molecular diagnosis, the rapid and accurate diagnosis of the animal and plant health inspection and quarantine has played a crucial part. Nowadays, the nucleic acid amplification by the polymerase chain reaction is acceptable. The molecular diagnosis based on polymerase chain reaction incorporated with specific primer sets for nucleic acid amplification has been demonstrated for accurate diagnosis of aquaculture diseases with a high sensitivity and specificity, such as RT-PCR, (Dhar et al., 2002, J. Virol. Methods 104, 69-82; Nishizawa et al., 1995, J. Gen. Virol. 76, 1563-1569), quantitative real-time PCR (DallaValle et al., 2005, Vet. Microbiol. 110, 167-179) or a conventional RT-PCR method (Nishizawa et al., 1995, J. Gen. Virol. 76, 1563-1569) that has been taken as the current "gold-standard method" for detection of NNV. The detection limit of 100-1000 copies of in vitro transcribed viral RNA in the RT-PCR assay has been demonstrated (Grotmol et al., 2000, Dis. Aquat. Organ. 39, 79-88).

However, there still exist some disadvantages, such as the need for an expensive and bulky thermal cycler, multiple and complex operating processes and low amplification efficiency (Mori et al., 2001, Biochem. Biophys. Res. Commun. 289, 150-154; Tomita et al., 2008, Nat. Protoc. 3, 877-882). Furthermore, test sample pre-treatment still remains a technically demanding and time-consuming step. The quality of RNA extraction could affect the results of the RNA-virus diagnosis. A hot phenol extraction or RNA purification kits are common methods for RNA purification and separation. In addition, the requirements for PCR-based platforms are technically demanding such as the precise temperature control necessary during the thermal cycling with the temperature variation ranging from 42° C. to 95° C., which is commonly performed by costly and bulky apparatus. In addition, the lengthy and costly diagnostic processes always need to be performed by well-trained personnel and the inaccuracy of the diagnosis may be attributed to these manual operations.

Accordingly, "isothermal amplification techniques," which allow exponential amplification of target nucleic acids at a constant and low temperature, has been developed for rapid detection of target DNA sequences (Piepenburg et al., 2006, PLoS Biol. 4, e204; Starkey et al., 2004, Dis. Aquat. Organ. 59, 93-100; Walker et al., 1994, Nucleic Acids Res. 22, 2670-2677). Among them, the loop-mediated-isothermal-amplification (LAMP) technique has attracted considerable interests as a potentially rapid, accurate, and cost-effective method for nucleic acid amplification. Specific nucleic acid sequences in the target test samples can be amplified by using four designated primers with the incorporation of Bst DNA polymerase, which is capable of high strand displacement under isothermal conditions (about 60° C.-65° C.) (Notomi et al., 2000, Nucleic Acids Res. 28, e63). Three major steps including an initial step, a cycling amplification step and an elongation step are conducted under a constant thermal condition and efficient amplification can be achieved since there is no time required for temperature ramping during the LAMP process (Nagamine et al., 2002, Mol. Cell. Probes 16, 223-229). In addition, the final amplified stem-loop DNAs consisting of cauliflower-like structures with multiple loops yields an amplification of $10^9$ copies of target DNA molecules, so that approximately a 100-fold greater sensitivity for LAMP amplification is demonstrated when compared with a conventional PCR process. As a consequence, a new diagnostic strategy incorporated the LAMP technique for fast and accurate detection of target genes has been demonstrated. For example, a LAMP-based detection of *Edwardsiella tarda* from infected Japanese flounder has been reported by targeting the haemolysin gene (Sayan et al., 2004, Appl. Environ. Microbiol. 70, 621-624). Another two-step RT-LAMP protocol for identification of the G-protein associated with the infectious haematopoietic necrosis virus (IHNV) in fish was also developed (Gunimaladevi et al., 2005, Arch. Virol. 150, 899-909). Despite the attractiveness of the LAMP technique, there are still some potential drawbacks in developing rapid diagnostic devices utilizing these state-of-the-art laboratory techniques. The entire nucleic acid amplification process is still costly and labor-intensive which utilizes lab-scale equipment such as pipettes and bulky thermo-heaters with a relatively large amount of bio-test samples/reagents. More importantly, bio-test sample pre-treatment processes prior to analysis such as DNA/RNA extraction are always required and need to be performed by experienced personnel. Furthermore, there is a high risk of contamination of bio-test samples during the entire diagnostic process, which may hinder the practical applications in the field survey.

Therefore, there is a great need to develop an integrated test sample-to-answer system to carry out all the diagnostic processes with a high specificity and sensitivity, in an automatic manner.

SUMMARY OF THE INVENTION

The present invention provides an integrated microfluidic LAMP system for rapidly detecting a pathogen in animals or plants. It has the advantages of simplifying nucleic acid extraction and purification, constant temperature reaction, high specificity and high sensitivity and contributes to the immediate and rapid screening of the pathogens in animals or plants. The present invention uses a specific nucleic acid probe and LAMP system for the rapid diagnosis of a variety of pathogen detection in animals or plants with the high detection sensitivity, high specificity, low sample consumption, low energy consumption, low cost and short reaction time, and compared to conventional analytical techniques, it has the breakthrough development and market value.

The invention provides a primer set for loop-mediated isothermal amplification, which is selected from the group consisting of first to fourteenth primer sets, wherein:
the first primer set comprises primers comprising the sequences SEQ ID NOs. 1 to 4 or a sequence complementary thereof; the second primer set comprises primers comprising the sequences SEQ ID NOs. 6 to 9 or a sequence complementary thereof; the third primer set comprises primers comprising the sequences SEQ ID NOs. 11 to 14 or a sequence complementary thereof; the fourth primer set comprises primers comprising the sequences SEQ ID NOs. 16 to 19 or a sequence complementary thereof; the fifth primer set comprises primers comprising the sequences SEQ ID NOs. 21 to 24 or a sequence complementary thereof; the sixth primer set comprises primers comprising the sequences SEQ ID NOs. 26 to 29 or a sequence complementary thereof; the seventh primer set comprises primers comprising the sequences SEQ ID NOs. 31 to 34 or a sequence complementary thereof; the eighth primer set comprises primers comprising the sequences SEQ ID NOs. 36 to 39 or a sequence complementary thereof; the ninth primer set comprises primers comprising the sequences SEQ ID NOs. 41 to 44 or a sequence complementary thereof; the tenth primer set comprises primers comprising the sequences SEQ ID NOs. 46 to 49 or a sequence complementary thereof; the eleventh primer set comprises primers comprising the sequences SEQ ID NOs. 51 to 54 or a sequence complementary thereof; the twelfth primer set comprises primers comprising the sequences SEQ ID NOs. 56 to 59 or a sequence complementary thereof; the thirteenth primer set comprises primers comprising the sequences SEQ ID NOs. 61 to 64 or a sequence complementary thereof; and the fourteenth primer set comprises primers comprising the sequences SEQ ID NOs. 66 to 69 or a sequence complementary thereof.

The invention also provides a probe comprising the sequence selected from the group consisting of SEQ ID NOs. 5, 10, 15, 20, 25, 30, 35, 40, 45, 50, 55, 60, 65, and 70, or a sequence complementary thereof.

The invention also provides a method for detecting a pathogen in animals or plants, which comprises conducting loop-mediated isothermal amplification with at least one primer set as mentioned above and a nucleic acid in a test sample, and if at least one amplification is carried out, the test sample comprises the pathogen in animals or plants.

The invention also provides a kit for detecting a pathogen in animals or plants comprising the primer set as mentioned above.

DETAILED DESCRIPTION OF THE INVENTION

Figure 1:
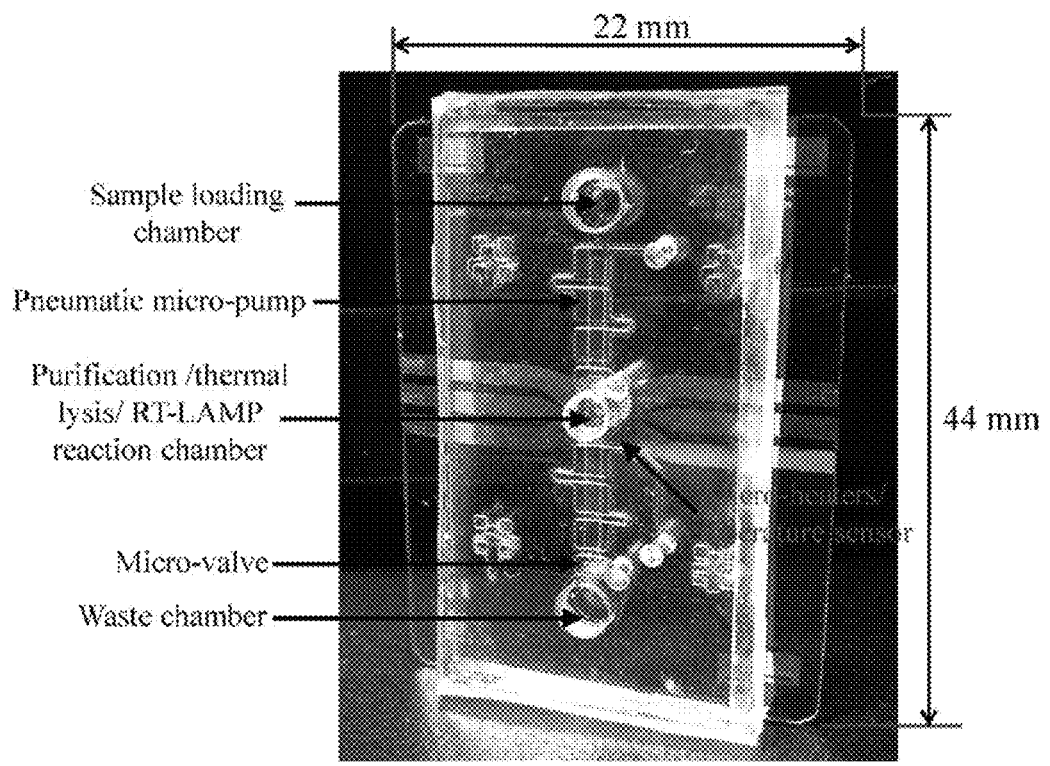
FIG. 1 illustrates a photograph of the integrated microfluidic LAMP system integrated with a microfluidic control module and the nucleic acid amplification module. The dimensions of the microfluidic chip are measured to be 44 mm×22 mm.

The invention provides a primer set for loop-mediated isothermal amplification, which is selected from the group consisting of first to fourteenth primer sets, wherein:
the first primer set comprises primers comprising the sequences SEQ ID NOs. 1 to 4 or a sequence complementary thereof; the second primer set comprises primers comprising the sequences SEQ ID NOs. 6 to 9 or a sequence complementary thereof; the third primer set comprises primers comprising the sequences SEQ ID NOs. 11 to 14 or a sequence complementary thereof; the fourth primer set comprises primers comprising the sequences SEQ ID NOs. 16 to 19 or a sequence complementary thereof; the fifth primer set comprises primers comprising the sequences SEQ ID NOs. 21 to 24 or a sequence complementary thereof; the sixth primer set comprises primers comprising the sequences SEQ ID NOs. 26 to 29 or a sequence complementary thereof; the seventh primer set comprises primers comprising the sequences SEQ ID NOs. 31 to 34 or a sequence complementary thereof; the eighth primer set comprises primers comprising the sequences SEQ ID NOs. 36 to 39 or a sequence complementary thereof; the ninth primer set comprises primers comprising the sequences SEQ ID NOs. 41 to 44 or a sequence complementary thereof; the tenth primer set comprises primers comprising the sequences SEQ ID NOs. 46 to 49 or a sequence complementary thereof; the eleventh primer set comprises primers comprising the sequences SEQ ID NOs. 51 to 54 or a sequence complementary thereof; the twelfth primer set comprises primers comprising the sequences SEQ ID NOs. 56 to 59 or a sequence complementary thereof; the thirteenth primer set comprises primers comprising the sequences SEQ ID NOs. 61 to 64 or a sequence complementary thereof; and the fourteenth primer set comprises primers comprising the sequences SEQ ID NOs. 66 to 69 or a sequence complementary thereof.

As utilized in accordance with the present disclosure, the following terms, unless otherwise indicated, shall be understood to have the following meanings:

The term "oligonucleotide" as referred to herein means single-stranded or double-stranded nucleic acid polymers of at least 10 bases in length. In certain embodiments, the nucleotides comprising the oligonucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phosphoraniladate and phosphoroamidate. The term "oligonucleotide" specifically includes single and double stranded forms of DNA.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "a sequence complementary" as used herein refers to a nucleic acid molecule able to be hybridized to the primer or probe according to the invention; preferably, refers to a nucleic acid molecule able to be completely hybridized to the primer or probe according to the invention.

The first primer set according to the invention is designed according to Mx protein. SEQ ID No. 1 is a forward primer of an outer primer pair; SEQ ID No. 2 is a reversed primer of the outer primer pair; SEQ ID No. 3 is a forward primer of an inner primer pair; and SEQ ID No. 4 is a reversed primer of the inner primer pair.

The second primer set according to the invention is designed according to *Vibrio* spp. SEQ ID No. 6 is a forward primer of an outer primer pair; SEQ ID No. 7 is a reversed primer of the outer primer pair; SEQ ID No. 8 is a forward primer of an inner primer pair; and SEQ ID No. 9 is a reversed primer of the inner primer pair.

The third primer set according to the invention is designed according to Infectious Laryngotracheitis virus (ILTV). SEQ ID No. 11 is a forward primer of an outer primer pair; SEQ ID No. 12 is a reversed primer of the outer primer pair; SEQ ID No. 13 is a forward primer of an inner primer pair; and SEQ ID No. 14 is a reversed primer of the inner primer pair. Preferably, the third primer set further comprises a helper forward primer of SEQ ID NO. 75 and a helper reversed primer of SEQ ID NO. 76.

The fourth primer set according to the invention is designed according to newcastle disease virus (NDV). SEQ ID No. 16 is a forward primer of an outer primer pair; SEQ ID No. 17 is a reversed primer of the outer primer pair; SEQ ID No. 18 is a forward primer of an inner primer pair; and SEQ ID No. 19 is a reversed primer of the inner primer pair.

The fifth primer set according to the invention is designed according to avian reovirus (ARV). SEQ ID No. 21 is a forward primer of an outer primer pair; SEQ ID No. 22 is a reversed primer of the outer primer pair; SEQ ID No. 23 is a forward primer of an inner primer pair; and SEQ ID No. 24 is a reversed primer of the inner primer pair. Preferably, the fifth primer set further comprises a helper forward primer of SEQ ID NO. 77 and a helper reversed primer of SEQ ID NO. 78.

The sixth primer set according to the invention is designed according to avian influenza virus (AIV). SEQ ID No. 26 is a forward primer of an outer primer pair; SEQ ID No. 27 is a reversed primer of the outer primer pair; SEQ ID No. 28 is a forward primer of an inner primer pair; and SEQ ID No. 29 is a reversed primer of the inner primer pair. Preferably, the sixth primer set further comprises a helper forward primer of SEQ ID NO. 79 and a helper reversed primer of SEQ ID NO. 80.

The seventh primer set according to the invention is designed according to Cucumber mosaic virus (CMV). SEQ ID No. 31 is a forward primer of an outer primer pair; SEQ ID No. 32 is a reversed primer of the outer primer pair; SEQ ID No. 33 is a forward primer of an inner primer pair; and SEQ ID No. 34 is a reversed primer of the inner primer pair.

The eighth primer set according to the invention is designed according to Tobacco mosaic virus (TMV). SEQ ID No. 36 is a forward primer of an outer primer pair; SEQ ID No. 37 is a reversed primer of the outer primer pair; SEQ ID No. 38 is a forward primer of an inner primer pair; and SEQ ID No. 39 is a reversed primer of the inner primer pair.

The ninth primer set according to the invention is designed according to *Pectobacterium carotovorum* subsp. *Carotovorum*. SEQ ID No. 41 is a forward primer of an outer primer pair; SEQ ID No. 42 is a reversed primer of the outer primer pair; SEQ ID No. 43 is a forward primer of an inner primer pair; and SEQ ID No. 44 is a reversed primer of the inner primer pair.

The tenth primer set according to the invention is designed according to *Acidovorax avenae* subsp. *citrulli*. SEQ ID No. 46 is a forward primer of an outer primer pair; SEQ ID No. 47 is a reversed primer of the outer primer pair; SEQ ID No. 48 is a forward primer of an inner primer pair; and SEQ ID No. 49 is a reversed primer of the inner primer pair.

The eleventh primer set according to the invention is designed according to Cymbidium mosaic virus (CymMV). SEQ ID No. 51 is a forward primer of an outer primer pair; SEQ ID No. 52 is a reversed primer of the outer primer pair; SEQ ID No. 53 is a forward primer of an inner primer pair; and SEQ ID No. 54 is a reversed primer of the inner primer pair. Preferably, the eleventh primer set further comprises a helper reversed primer of SEQ ID NO. 71.

The twelfth primer set according to the invention is designed according to Odontoglossum ringspot virus (ORSV). SEQ ID No. 56 is a forward primer of an outer primer pair; SEQ ID No. 57 is a reversed primer of the outer primer pair; SEQ ID No. 58 is a forward primer of an inner primer pair; and SEQ ID No. 59 is a reversed primer of the inner primer pair. Preferably, the twelfth primer set further comprises a helper reversed primer of SEQ ID NO. 72.

The thirteenth primer set according to the invention is designed according to Tomato spotted wilt virus (TSWV). SEQ ID No. 61 is a forward primer of an outer primer pair; SEQ ID No. 62 is a reversed primer of the outer primer pair; SEQ ID No. 63 is a forward primer of an inner primer pair; and SEQ ID No. 64 is a reversed primer of the inner primer pair. Preferably, the thirteenth primer set further comprises a helper reversed primer of SEQ ID NO. 73.

The fourteenth primer set according to the invention is designed according to Capsicum chlorosis virus (CaCV). SEQ ID No. 66 is a forward primer of an outer primer pair; SEQ ID No. 67 is a reversed primer of the outer primer pair; SEQ ID No. 68 is a forward primer of an inner primer pair; and SEQ ID No. 69 is a reversed primer of the inner primer pair. Preferably, the fourteenth primer set further comprises a helper reversed primer of SEQ ID NO. 74.

The primer set according to the invention can be applied in loop-mediated isothermal amplification to detection the existence of a pathogen in animals or plants, and the kind of the pathogen in animals or plants can be further identified and disease control and prevention are provided early.

Each of the inner primer pair and outer primer pair of the first to fourteenth primer sets according to the invention can be reacted under one condition, and no cross reactions occur between each other, and the sensitivity and specificity are both high.

In one preferred embodiment of the invention, hybridization and loop-mediated isothermal amplification can be applied simultaneously for detecting a pathogen in animals or plants more rapidly and accurately.

Therefore, the invention also provides a probe comprising the sequence selected from the group consisting of SEQ ID NOs. 5, 10, 15, 20, 25, 30, 35, 40, 45, 50, 55, 60, 65, and 70, or a sequence complementary thereof.

The probe encoded by SEQ ID NO. 5 according to the invention is designed according to Mx protein.

The probe encoded by SEQ ID NO. 10 according to the invention is designed according to *Vibrio* spp.

The probe encoded by SEQ ID NO. 15 according to the invention is designed according to Infectious Laryngotracheitis virus (ILTV).

The probe encoded by SEQ ID NO. 20 according to the invention is designed according to newcastle disease virus (NDV).

The probe encoded by SEQ ID NO. 25 according to the invention is designed according to avian reovirus (ARV).

The probe encoded by SEQ ID NO. 30 according to the invention is designed according to avian influenza virus (AIV).

The probe encoded by SEQ ID NO. 35 according to the invention is designed according to Cucumber mosaic virus (CMV).

The probe encoded by SEQ ID NO. 40 according to the invention is designed according to Tobacco mosaic virus (TMV).

The probe encoded by SEQ ID NO. 45 according to the invention is designed according to *Pectobacterium carotovorum* subsp. *Carotovorum*.

The probe encoded by SEQ ID NO. 50 according to the invention is designed according to *Acidovorax avenae* subsp. *citrulli*.

The probe encoded by SEQ ID NO. 55 according to the invention is designed according to Cymbidium mosaic virus (CymMV).

The probe encoded by SEQ ID NO. 60 according to the invention is designed according to Odontoglossum ringspot virus (ORSV).

The probe encoded by SEQ ID NO. 65 according to the invention is designed according to Tomato spotted wilt virus (TSWV).

The probe encoded by SEQ ID NO. 70 according to the invention is designed according to Capsicum chlorosis virus (CaCV).

The principle of probe design is the location sequence of the probe having infrequent variation occurred, and:

1. the length of the probe is preferred between 17 to 27 nucleotides, and if the probe is too short, it causes a difficult target DNA binding; if the probe is too long, non-specific hybridization occurs easily;

2. the G+C ratio is between 40% to 60% to lowered the probability of secondary structure;

3. the Tm (melting temperature) is designed as much as possible at the hybridization temperature±5° C.; for example, if the hybridization temperature is designed at 50° C., the Tm of the probe should be as much as possible at 45° C. to 55° C.;

4. hairpin loops, palindrome, and repeats are avoided as much as possible;

5. a mismatch is designed in the middle position of the whole probe, and 8 and 10 thymines are added at the 3'-end of the probe to facilitate the binding between the probe and a nylon membrane.

A designed probe is subjected to BLAST to make sure that no sequence similarity with other species in GenBank for avoiding cross hybridization.

The term "a probe" as used herein refers to a nucleic acid molecule containing at least 8 consecutive nucleotides; preferably 10 to 50 consecutive nucleotides; more preferably 15 to 40 consecutive nucleotides; most preferably 17 to 27 consecutive nucleotides. In another aspect, 8 and 10 thymines are preferably contained at the 3'-end of the probe. The probe can be applied in hybridization under a hybridization condition with a target DNA. The hybridization condition can be set by artisans skilled in the field, and preferably between about 40° C. to about 65° C.

To sum up, the primer sets and probes according to the invention are listed in Table 1:

TABLE 1

| SEQ ID No. | Name | Sequence |
|---|---|---|
| 1 | Mx-F3 | GGTCATGGTCAAGGAGCAG |
| 2 | Mx-B3 | GCTCCATCTTGAACTGGGTC |
| 3 | Mx-FIP | GGCCAGCTGTATGAACGCCTTCTTTTTTCAAACAGCTGGAGGAACC |
| 4 | Mx-BIP | CAGCGAAGGCCAAGATTGAAGCTTTTTCTCAGCATGGATTCAGCAGT |
| 5 | Mx-probe | TTTTTTTTTTCAGCTTTCACTCAGGATGCCA |
| 6 | Vib-F3 | TCATTCCAGATTGGTGCGAG |
| 7 | Vib-B3 | CGCCATCTTTGGCTAACACA |
| 8 | Vib-FIP | TGCAAGGAACGATTGGCCGCTTTTTCATTATGGGGCTTACCAGCA |
| 9 | Vib-BIP | AAGGACAAGGATTGGGGAGTGCTTTTTAACAAGCTCACCTGCCTG |
| 10 | Vib-probe | TTTTTTTTTTATCAGCAAACGGCACCAACTC |
| 11 | ILTV-F3 | GCAAAATGTTCACGGGGA |
| 12 | ILTV-B3 | TCTACTGCGTCAATTAAGCT |
| 13 | ILTV-FIP | GCTGGTAAGTAAAAAATGCACAAGTAAAACTGTACTTTCATTTGTGGT |
| 14 | ILTV-BIP | CGGAGGCATGTGCACTGAAATCGTTTGGTTGTAAGAGAACT |
| 15 | ILTV-probe | TTTTTTTTTTGGAAACGGTCGACTGGACGT |
| 16 | NDV-F3 | TCAAGGGCCTGTCTCACT |
| 17 | NDV-B3 | TCTAGGGTTCCACTCCCG |
| 18 | NDV-FIP | TGGGGTGCCTGCACTACTGAATGATGGTCACATGCGAGAA |
| 19 | NDV-BIP | CTGCAAAGCTGTAGGGTTGTGCTCTCTGGCGCTTTCACGT |
| 20 | NDV-probe | TTTTTTTTTTGCAAATCGCCCCGCAATATA |
| 21 | ARV-F3 | ACGCATATCCCATCAGACCT |
| 22 | ARV-B3 | AGGTGTCGATGCCGGTAC |
| 23 | ARV-FIP | GTCGCAGAATCGCGGGTGAATGTTCCTAGTGCGGGATTCCA |
| 24 | ARV-BIP | GGTGTACTCGAGCTCACGTGTCGTCAAGGAACGAATGTTCG |
| 25 | ARV-probe | TTTTTTTTTTCGGCGTGGTTTCATTAGACA |
| 26 | AIV-F3 | TCTAACCGAGGTCGAAACGT |
| 27 | AIV-B3 | CGTCTACGCTGCAGTCCT |
| 28 | AIV-FIP | TCGGTGTTCTTCCCTGCAAAGATTCTCTATCGTCCCGTCA |

TABLE 1-continued

| SEQ ID No. | Name | Sequence |
|---|---|---|
| 29 | AIV-BIP | TCGAGGCTCTCATGGAATGGCTAGCGTGAACACAAACCCTAA |
| 30 | AIV-probe | TTTTTTTTTTCTACTCAGCCGGTGCACTTG |
| 31 | CMV-F3 | CGCGCATTCAAATTCGAGTT |
| 32 | CMV-B3 | GGCGTACTTTCGCATGTCG |
| 33 | CMV-FIP | GGCGGCAACGGATAAGTCCGGATTCTACCGTGTGGGTGAC |
| 34 | CMV-BIP | ATCAGTATGCCGCATCCGGAGATCGCCGAGAGATCGTACA |
| 35 | CMV-probe | TTTTTTTTTTCCATGACTCAACTCAAACGTC |
| 36 | TMV-F3 | AACGACAGTTCAGTGAGG |
| 37 | TMV-B3 | AACGTTTCAGCGGTTGT |
| 38 | TMV-FIP | TTGTACCTGTACACCTTAAAGTCACTGGAAACCTTCACCCCAA |
| 39 | TMV-BIP | TGCAGTACTAGATCCTCTAATCACCCGCCTGATTTTCGACTTCT |
| 40 | TMV-probe | TTTTTTTTTTAAGTCTCCGAATCATCTCCGA |
| 41 | Pcc-F3 | CGTCAGGTTATCAAAGCCCA |
| 42 | Pcc-B3 | TGCCAGTGAACATCGTGAC |
| 43 | Pcc-FIP | TGTTTCGGCACCAGACGGAACGGCAGCACAGGAAATCCT |
| 44 | Pcc-BIP | GCGTTCCATGATGGATCGCGTATGCACTGTTCAACGCACAA |
| 45 | Pcc-probe | TTTTTTTTTTTCAGTGCTCTGTTGCAGAGT |
| 46 | Aa-F3 | TCATTACATTGCGCGGAACT |
| 47 | Aa-B3 | CGGTCGCCAGAAAAATCCT |
| 48 | Aa-FIP | TTCCAGCGATAGGGCGACATGATTACCTCGAAGACCCCGTT |
| 49 | Aa-BIP | GTTTCGGCACAGGGCGACCGCAGGCCCAAACCGTCT |
| 50 | Aa-probe | TTTTTTTTTGATTTCATCCAGAGAGCCAAC |
| 51 | CymMV-F3 | TGGTCCAGCTATTCACCGG |
| 52 | CymMV-B3 | CGGAGTCAGTGTCATCCTCAG |
| 53 | CymMV-FIP | CGCACGTGTATGGATGGTCTCTAAGCTCTCGACTGGCAAAC |
| 54 | CymMV-BIP | CGCTTCGCATGTGCAGAGACCCGTCAGGGAGCTGTCTGA |
| 55 | CymMV-probe | TTTTTTTTTTCCACAGGGTCAAAAGGTC |
| 56 | ORSV-F3 | ATACTGCCGAACTTGTAGT |
| 57 | ORSV-B3 | ACTCATCTTGAGGACTGAGA |
| 58 | ORSV-FIP | GGCATCTGAAGTCATCGGTGTAGGGATGCTTACATTATTGACG |
| 59 | ORSV-BIP | TCACAGGTGGATGGCTAAGCTGTATTGATCAATAGCGGGTAA |
| 60 | ORSV-probe | TTTTTTTTTTCGAACTGCTGCTGAACGTC |

TABLE 1-continued

| SEQ ID No. | Name | Sequence |
|---|---|---|
| 61 | TSWV-F3 | CATGACCTTCAGAAGGCT |
| 62 | TSWV-B3 | AGACAACACTGATCATCTCA |
| 63 | TSWV-FIP | GGTGGGAAGCAATCTTAGATTTGATCTTGATCAGGGTCAGGCT |
| 64 | TSWV-BIP | ATGGATTACCTCTTGATGATGCAACTGAAGCAATAAGAGGTAAGC |
| 65 | TSWV-probe | TTTTTTTTTTGCTTTGCTTTTCAGCACGG |
| 66 | CaCV-Ph-F3 | GCACAAGAATGATATACAGATGA |
| 67 | CaCV-Ph-B3 | GAGTGTATAATGATGTATGTAAAGC |
| 68 | CaCV-Ph-FIP | TGGAACTTCACTATCTGTCTTGACATTCAAGTTCCCTTGAAGCC |
| 69 | CaCV-Ph-BIP | GATCCGTATTCTGTTTGTCCTCTTTTAAGAGAGTTTGCATTCCTAC |
| 70 | CaCV-Ph-probe | TTTTTTTTTTGCCATATCTGACTTTCATGAATGTTC |
| 71 | CymMV-LB | TACCATGCGATGAATATGATCGTG |
| 72 | ORSV-LB | ATTGGTCAATTAGCTGATTTTGAC |
| 73 | TSWV- LB | GGCTTGCCATAATGCTGGGAGG |
| 74 | CaCV-Ph-LB | CACGTTCCCAGTATCAATGAACT |
| 75 | ILTV-LF | AATACCGTCGCGAGTTTTTGA |
| 76 | ILTV-LB | TGTTTAGAGTTTGCCGAGACG |
| 77 | ARV-LF | TACGTCCACAGGGAACGAC |
| 78 | ARV-LB | TTACTTTCCCAACCGGAGGT |
| 79 | AIV- LF | ATCTCGGCTTTGAGGGGGC |
| 80 | AIV-LB | AAGACCAATCCTGTCACCTCTGACT |

The invention also provides a method for detecting a pathogen in animals or plants, which comprises conducting loop-mediated isothermal amplification with at least one primer set as mentioned above and a nucleic acid in a test sample, and if at least one amplification is carried out, the test sample comprises the pathogen in animals or plants.

In one preferred embodiment of the invention, the method is further used for detecting the kind of the pathogen in animals or plants.

If the test sample is derived from a fish, and if the amplification is carried out with the nucleic acid in the test sample and the first primer set, the fish is infected and expresses Mx protein.

If the amplification is carried out with the nucleic acid in the test sample and the second primer set, the pathogen comprises *Vibrio* spp.

If the amplification is carried out with the nucleic acid in the test sample and the third primer set, the pathogen comprises Infectious Laryngotracheitis virus (ILTV).

If the amplification is carried out with the nucleic acid in the test sample and the fourth primer set, the pathogen comprises newcastle disease virus (NDV).

If the amplification is carried out with the nucleic acid in the test sample and the fifth primer set, the pathogen comprises avian reovirus (ARV).

If the amplification is carried out with the nucleic acid in the test sample and the sixth primer set, the pathogen comprises avian influenza virus (AIV).

If the amplification is carried out with the nucleic acid in the test sample and the seventh primer set, the pathogen comprises Cucumber mosaic virus (CMV).

If the amplification is carried out with the nucleic acid in the test sample and the eighth primer set, the pathogen comprises (Tobacco mosaic virus (TMV).

If the amplification is carried out with the nucleic acid in the test sample and the ninth primer set, the pathogen comprises *Pectobacterium carotovorum* subsp. *Carotovorum*.

If the amplification is carried out with the nucleic acid in the test sample and the tenth primer set, the pathogen comprises *Acidovorax avenae* subsp. *citrulli*.

If the amplification is carried out with the nucleic acid in the test sample and the eleventh primer set, the pathogen comprises Cymbidium mosaic virus (CymMV).

If the amplification is carried out with the nucleic acid in the test sample and the twelfth primer set, the pathogen comprises Odontoglossum ringspot virus (ORSV).

If the amplification is carried out with the nucleic acid in the test sample and the thirteenth primer set, the pathogen comprises Tomato spotted wilt virus (TSWV).

If the amplification is carried out with the nucleic acid in the test sample and the fourteenth primer set, the pathogen comprises Capsicum chlorosis virus (CaCV).

The test sample according to the present invention may contain pathogenic culture to be identified, specimen from the animals or plants, or a sample of the nucleic acid information further derived from the pathogenic culture to be identified or specimen from the animals or plants; wherein the specimen from the animals or plants is preferably the blood, muscle or brain tissue.

In one preferred embodiment of the invention, the product of the loop-mediated isothermal amplification in the sample is marked. The manner of marking the product of the loop-mediated isothermal amplification is known to artisans skilled in the art. For example, when conducting the loop-mediated isothermal amplification, the primer comprises a marker, and preferably, the marker is digoxigenin, or a marked dUTP can be used for introducing a marker in the product.

In one preferred embodiment of the invention, the method further comprises a positive control step. Any determined primers for identifying a determined fragment are suitable for the positive control step.

In one preferred embodiment of the invention, the method further comprises conducting hybridization with at least one probe and the nucleic acid in the test sample, wherein the at least one probe comprises the sequence selected from the group consisting of SEQ ID NOs. 5, 10, 15, 20, 25, 30, 35, 40, 45, 50, 55, 60, 65, and 70, or a sequence complementary thereof.

In one preferred embodiment of the invention, the at least one probe is linked to a magnetic bead.

According to the invention, the magnetic bead and the at least one probe linked thereon are designed for purifying the nucleic acid in the test sample to facilitate the following operations. Artisans skilled in the field of the invention can choose an appropriate material and size of the magnetic bead. In one preferred embodiment of the invention, the diameter of the magnetic bead is from about 1 µm to about 5.0 µm. Such range both facilitates the linkage between the magnetic bead and the at least one probe and the following operations.

According to the invention, the manner for linking the at least one probe to the magnetic bead is well-known to artisans skilled in the field of the invention according to the disclosure of the specification of the invention. A conventional manner of linking an oligonucleotide to a magnetic bead can be applied in the invention. In one preferred embodiment of the invention, the magnetic bead is linked to the at least one probe through an amide bond or a carboxylate bond.

According to the invention, the at least one probe is designed for hybridizing the pathogenic nucleic acid in the test sample through a complementary feature. The hybridizing complex is further purified by the magnetic force. Moreover, the two hybridized strands can be separated in the subsequently loop-mediated isothermal amplification, and further amplified.

According to the invention, the reagents for loop-mediated isothermal amplification are well-known to artisans skilled in the field of the invention according to the disclosure of the specification of the invention. For example, the design described in Notomi et al, 2000, Nucleic Acids Res. 28, e63. Such disclosure is incorporated herein by reference.

In one preferred embodiment of the invention, the nucleic acid in the test sample is a RNA fragment, and the method further comprises conducting a reverse transcription polymerase chain reaction. It allows carrying on the reverse transcription polymerase chain reaction before the purification and amplification.

In one preferred embodiment of the invention, the method comprises the steps of:
(a) purifying the nucleic acid in the test sample with a magnetic bead;
(b) conducting loop-mediated isothermal amplification with the primer set and the nucleic acid in the step (a); and
(c) detecting a product of the loop-mediated isothermal amplification.

The invention also provides a kit for detecting a pathogen in animals or plants comprising the primer set as mentioned above.

In one preferred embodiment of the invention, the kit further comprises at least one probe as mentioned above.

In one preferred embodiment of the invention, the kit further comprises a magnetic bead, and the magnetic bead is linked to the at least one probe.

In one preferred embodiment of the invention, the kit further comprises reagents for loop-mediated isothermal amplification.

In one preferred embodiment of the invention, the kit further comprises reagents for a reverse transcription polymerase chain reaction. It allows carrying on a reverse transcription polymerase chain reaction before the purification and amplification.

In one preferred embodiment of the invention, the kit further comprises a microfluidic chip. As used herein, "a microfluidic chip" refers to an apparatus that detection-required elements such as a test sample loading chamber, a pneumatic micro-pump, a reaction chamber, a micro-valve, and a waste chamber, are integrated thereon. The test sample or reagents are driven to move in micro-channels connecting the elements by electroosmotic flow generated by voltage applied or the use of micro-pumps or a centrifugal force to complete the reaction. The microfluidic chip also known as a lab-on-a-chip, and the use of microfluidic chip for biomedical detection or analysis has advantages of reduced manual error, increased system stability, reduced energy consumption and reduced amount of test samples, reduced the capacity and time-saving.

In one preferred embodiment of the invention, the microfluidic chip comprises a microfluidic control module and an isothermal amplification module is shown in FIG. 1. The microfluidic control module comprises one glass substrate with metallization patterns and two polydimethylsiloxane (PDMS) layers, namely a thick PDMS layer with structures for the microfluidic channel and a thin-film PDMS membrane for the air chambers. The microfluidic control module further comprises one test sample loading chamber, one purification/thermal lysis/LAMP reaction chamber, a waste chamber and two sets of pneumatic micro-pumps with normally-closed micro-valves. These valves are designed for liquid delivery and to prevent backflow in the miniature system. The optimal design parameters, microfabrication and characterizations for the module can be referenced of Yang et al., 2009 (Yang et al., 2009, Microfluid. Nanofluid. 6, 823-833). Such disclosure is incorporated herein by reference.

The isothermal amplification module of the microfluidic chip preferably comprises two sets of self-compensated, array-type micro-heaters and a temperature sensor is built to generate the temperature distribution with a high thermal uniformity within the thermal lysis/LAMP reaction chamber. Without using additional control circuits, the isothermal amplification module is fabricated with surrounding heating grids which are used as compensating heaters for the edge areas. Hence, the amplification efficiency of the LAMP process can be enhanced within the reaction chamber distributed with a high thermal uniformity. Details of the self-compensated, isothermal amplification module and the microfabrication process can be found in the previous literature (Hsieh et al., 2009, Microfluid. Nanofluid. 6, 797-809). Meanwhile, in one preferred embodiment of the invention, an application specific integrated circuit (ASIC) controller is used to control all the components including the microfluidic control module and the isothermal amplification module. A heat sink with a pocket for placement of a permanent magnet and an adjustable magnetic stage directly connected to a compressed gas tank regulated by the EMV are employed. The permanent magnet on the magnetic stage can be engaged and slided into the pocket automatically during the purification process by providing a digital signal into the EMV, followed by disengaging it from the pocket during the re-suspension and LAMP processes. Thus, the test sample transportation process and the temperature field distribution can be precisely and automatically controlled.

Preferably, the kit according to the invention further comprises an apparatus or a system for detecting the product of the amplification. In one preferred embodiment of the invention, the kit further comprises a gel electrophoresis system or an absorbance detection system for detecting a product of loop-mediated isothermal amplification.

In one preferred embodiment of the invention, in the amplification processes within LAMP, pyrophosphate is released, followed with nucleic acid elongation, and is reacted with magnesium ions to cause a change in turbidity in the mixture. Consequently, an optical system is integrated in the future to sense the turbidity variation for the amount of end product.

In one preferred embodiment of the invention, the kit further comprises a lysis buffer for lysing the test sample. More preferably, the lysis buffer is able to preliminarily lysing the test sample to facilitate the following purification and amplification.

In one preferred embodiment of the invention, the method provides the specific primer sets and probes for detecting common pathogens in animals or plants. First, the probe specific to the pathogen is linked to the magnetic bead. After lysing the cells, the pathgenic nucleic acids dissolved in the whole-tissue lysate in the test sample are specifically detected and hybridized on the surface of the magnetic bead. Hereafter, the combination of the built-in microfluidic control module and permanent magnet is applied to purify the magnetic complex from the test sample. In addition, the one-step isothermal LAMP is performed to amplify the target gene by the use of the isothermal amplification module of the chip. Thus, the kit and method according to the present invention provides an automated platform of a fast diagnosis of disease in aquaculture with little need of human intervention. The duration from extracting the nucleic acid to obtain the result is only 65 minutes, and the waiting time is significantly reduced. With this combination of the specific probes and the magnetic beads, the pathogenic nucleic acid can be captured directly, and the extraction and purification of nucleic acid are simplified. In another aspect, the primer set according to the invention can isothermally amplify the pathogenic nucleic acid, and is proven to have high specificity.

The minimum detection limit of the present invention can be lowered to 20 copies, that is about 1000 times higher than that of the conventional PCR, and the sensitivity is significantly increased. Furthermore, LAMP uses four primers to react, so that the specificity is higher than that of the conventional PCR, and the error rate is significantly reduced. Therefore, the method and kit according to the invention can be used for early detection to protect the species with a high economic value.

The following Examples are given for the purpose of illustration only and are not intended to limit the scope of the present invention.

Example

Experimental Procedures

The microfluidic chip shown in FIG. 1 is applied in the example. The nucleic acids of the pathogens are isolated by utilizing probe-conjugated magnetic beads, followed by performing the one-step isothermal amplification with the incorporation of built-in micro-heaters and temperature sensors. Briefly, a random sampling of the animals or plants is first carried out, followed by a grinding process with a pestle in an 1.5 mL microcentrifuge tube. The on-chip micro-heaters are then activated to perform the thermal lysis of the bio-test samples when the tissue fluid of the animals or plants is loaded into a purification chamber of the microfluidic chip.

Then, the hybridization of the released nucleic acids is performed by loading the specific probe-conjugated, magnetic beads into the purification chamber at 55° C. to 65° C. Next, a permanent magnet is attached underneath the chip to attract the hybridized nucleic acid-probe-conjugated magnetic complexes onto the surface of the purification chamber, followed by flowing a washing buffer through the purification chamber continuously using an integrated micro-pump. All the other unbound interferents in the biological solution would then be washed away into a waste chamber. The LAMP reagents are then loaded into a test sample loading chamber, followed by transporting them into the purification chamber to perform the subsequent synthesization of target gene and isothermal amplification simultaneously. With this approach, the pathogenic nucleic acid can be isolated from the biological tissues and then are used in the subsequent identification of genetic patterns associated with aquaculture diseases.

Detailed procedure is illustrated below.

Infectious Test Samples Preparation

The infected animals or plants are first sampled randomly and collected from cultivation farms. All the samples are stored at −80° C. prior to the pathogenic nucleic acid extraction process and the on-chip analysis. To avoid the clogging of the micro channels by large or tough tissue, the organs are grinded using a tissue grinder to obtain virus particles from extracted test samples.

Probe and Primers Design

The primers and probes are designed by selecting Mx protein, *Vibrio* spp., Infectious Laryngotracheitis virus (ILTV), newcastle disease virus (NDV), avian reovirus (ARV), avian influenza virus (AIV), Cucumber mosaic virus (CMV), Tobacco mosaic virus (TMV), *Pectobacterium carotovorum* subsp. *Carotovorum, Acidovorax avenae* subsp. *citrulli*, Cymbidium mosaic virus (CymMV), Odontoglossum ringspot virus (ORSV), Tomato spotted wilt virus (TSWV), and Capsicum chlorosis virus (CaCV) by using Eiken Genome site (http://primerexplorer.jp/elamp3.0.0/index.html) and Primer3 (http://frodo.wi.mit.edu/primer3/). The sequences are listed in Table 1.

Magnetic Bead-Based RNA1 Extraction and Hybridization

A specific probe is conjugated onto the surface of the magnetic beads (MAGBEAD AGT-003-05, Applied gene technologies technologies, USA) by utilizing the carboxylated linkage prior to the on-chip analysis (Hawkins et al., 1994, Nucleic Acids Res. 22, 4543-4544). A grinding process is first performed by using a pestle with a 200 μL of lysis buffer [62.5 mM Tris, pH8.3, 95 mM KCl, 3.8 mM $MgCl_2$, 12.5 mM dithiothreitol (DTT), and 0.63% octyl phenoxylpoly ethoxylethanol (NP-40)] in an 1.5 mL microcentrifuge tube to collect the whole tissue lysates. Then, 25 μL of whole tissue lysates is then loaded into the purification chamber, where the pathogenic nucleic acid-specific probe-conjugated magnetic beads with a volume of 10 μL are pre-loaded, to perform the thermal lysis process of the virus at 90° C. to 97° C. for 5 to 10 min. After that, a temperature field of 55° C. to 65° C. for 15 min is generated within the purification chamber for the hybridization process between the pathogenic nucleic acid and the specific probe-conjugated magnetic beads. Then, a magnetic field (~300 Gauss) generated by a permanent magnet is used to concentrate and to collect the nucleic acid-bound magnetic complexes onto the surface of the purification chamber, followed by washing all the other biological substances away into the waste chamber with the incorporation of micro-pumps and micro-valves. Next, the LAMP reagents are introduced into the reaction for the subsequent one-step LAMP process by the micro-pumps.

One-Step LAMP

A final reaction volume of 25 μL is employed for the one-step RT-LAMP process and the LAMP reaction is modified as previously described (Notomi et al., 2000, Nucleic Acids Res. 28, e63). The reaction mixture is listed in Table 2.

TABLE 2

| Grouper | Vol. (μL) | Avian | Vol. (μL) | Plant-seedlings | Vol. (μL) | Orchid | Vol. (μL) |
|---|---|---|---|---|---|---|---|
| RT Reagent |  | LAMP |  | Genomic DNA | 1 | 5M betaine | 4 |
| RNA | 5 | LAMP buffer | 2.5 | 2.5 mM dNTP | 4 | LAMP buffer | 2.5 |
| Random primer | 1 | 10 mM dNTP | 2.5 | LAMP buffer | 2.5 | 100 mM $MgSO_4$ | 1.5 |
| DEPC treated water | 9 | 100 mM $MgSO_4$ | 2.5 | F3 (10 μM) | 0.5 | 25 mM dNTP | 1.4 |
| RT buffer | 5 | 5M betaine | 2.5 | B3 (10 μM) | 0.5 | 100 mM DTT | 1.3 |
| RTase | 1 | F3/B3 primer (5 μM) | 2 | FIP (10 μM) | 2 | dd water | 2 |
| 2.5 mM dNTP | 4 | FIP/BIP primer (5 μM) | 8 | BIP (10 μM) | 2 | 5 pmol F3 | 1 |
|  |  | LF/LB primer (5 μM) | 2 | dd water | 11.5 | 5 pmol B3 | 1 |
| LAMP Reagent |  | DNA | 2 | Taq | 0.4 | 40 pmol FIP | 1 |
| cDNA | 1 | Bst | 1 |  |  | 40 pmol BIP | 1 |
| dd water | 11.5 |  |  | RT-LAMP |  | 20 pmol LF | 1 |
|  |  | RT-LAMP |  | RNA | 1 | 20 pmol LB | 1 |

TABLE 2-continued

| Grouper | Vol. (μL) | Avian | Vol. (μL) | Plant-seedlings | Vol. (μL) | Orchid | Vol. (μL) |
|---|---|---|---|---|---|---|---|
| | | LAMP buffer | 2.5 | F3 (10 μM) | 0.5 | Bst | 1 |
| | | 10 mM dNTP | 2.5 | B3 (10 μM) | 0.5 | AMV | 0.1 |
| | | 100 mM MgSO₄ | 2.5 | FIP (10 μM) | 2 | RNase OUT | 0.2 |
| | | 5M betaine | 2.5 | BIP (10 μM) | 2 | RNA | 5 |
| | | F3/B3 primer (5 μM) | 2 | 2.5 mM dNTP | 4 | | |
| | | FIP/BIP primer (5 μM) | 8 | dd water | 10 | | |
| | | RTase | 1 | Bst | 1 | | |
| | | RNA | 3 | RTase | 0.5 | | |
| | | Bst | 1 | | | | |

The reaction mixture is loaded in the LAMP reaction chamber for the isothermal amplification at 60° C. The LAMP products are analyzed by slab-electrophoresis technique in a 2% agarose gel.

In addition, in order to ensure accuracy of the present invention, a negative control of using ddH$_2$O instead of the sample.

Figure 2:
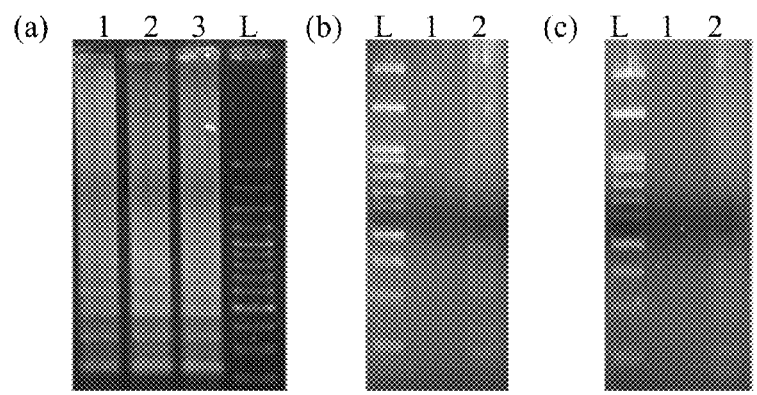
FIG. 2 shows that the method according to the invention can detect three pathogens and an anti-virus protein of groupers by the LAMP; (a) nervous necrosis virus, Lane 1: 75 minutes; Lane 2: 60 minutes; Lane 3: 45 minutes; Lane L: 100 bp DNA ladder marker; (b) Mx, Lane L: 100 bp DNA ladder marker; Lane 1: negative control (dd $H_2O$); Lane 2: test sample; (c) *Vibrio* spp., Lane L: 100 bp DNA ladder marker; Lane 1: negative control (dd $H_2O$); Lane 2: test sample.
Figure 3:
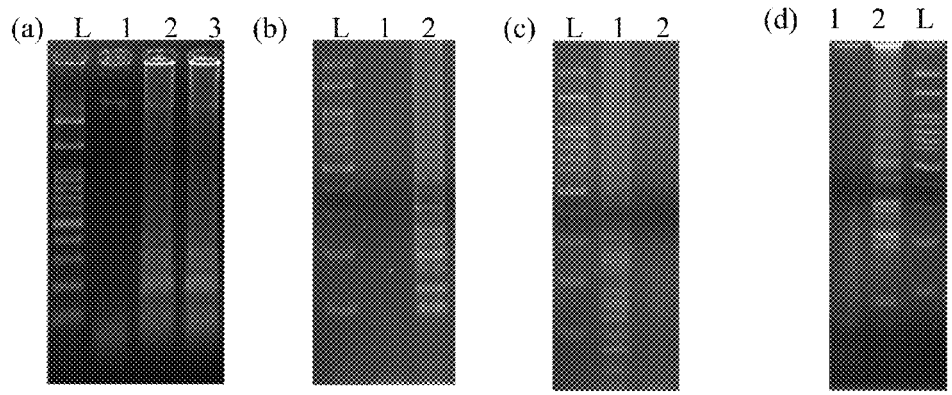
FIG. 3 shows that the method according to the invention can detect four pathogens of avians by the LAMP or RT-LAMP; (a) Infectious Laryngotracheitis virus, Lane L: 100 bp DNA ladder marker; Lane 1: negative control (dd $H_2O$); Lanes 2 and 3: test sample (DNA); (b) newcastle disease virus, Lane L: 100 bp DNA ladder marker; Lane 1: negative control (dd $H_2O$); Lane 2: test sample; (c) avian reovirus, Lane L: 100 bp DNA ladder marker; Lane 1: test sample (RNA); Lane 2: negative control (dd $H_2O$); (d) avian influenza virus, Lane L: 100 bp DNA ladder marker; Lane 1: negative control (dd $H_2O$); Lane 2: test sample (RNA).
Figure 4:
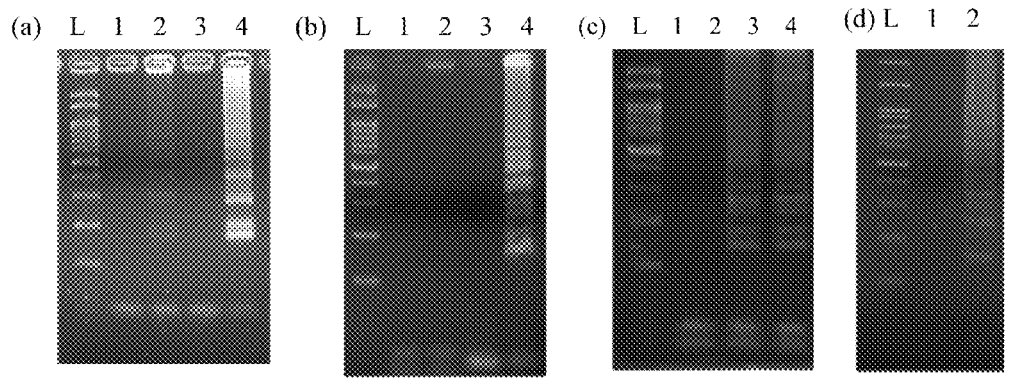
FIG. 4 shows that the method according to the invention can detect four pathogens of plant seedlings by the LAMP; (a) Cucumber mosaic virus, Lane L: 100 bp DNA ladder marker; Lane 1: conventional negative control; Lane 2: conventional test sample; Lane 3: microfluidic negative control; Lane 4: microfluidic test sample; (b) *Pectobacterium carotovorum* subsp. *Carotovorum*, Lane L: 100 bp DNA ladder marker; Lane 1: Aa negative control (dd $H_2O$); Lane 2: Aa test sample; Lane 3: Pcc negative control (dd $H_2O$); Lane 2: Pcc test sample; (c) *Acidovorax avenae* subsp. *citrulli*, Lane L: 100 bp DNA ladder marker; Lane 1: negative control; Lane 2: test sample 1; Lane 3: test sample 2; (d) Tobacco mosaic virus, Lane L: 100 bp DNA ladder marker; Lane 1: negative control; Lane 2: test sample (RNA).
Figure 5:
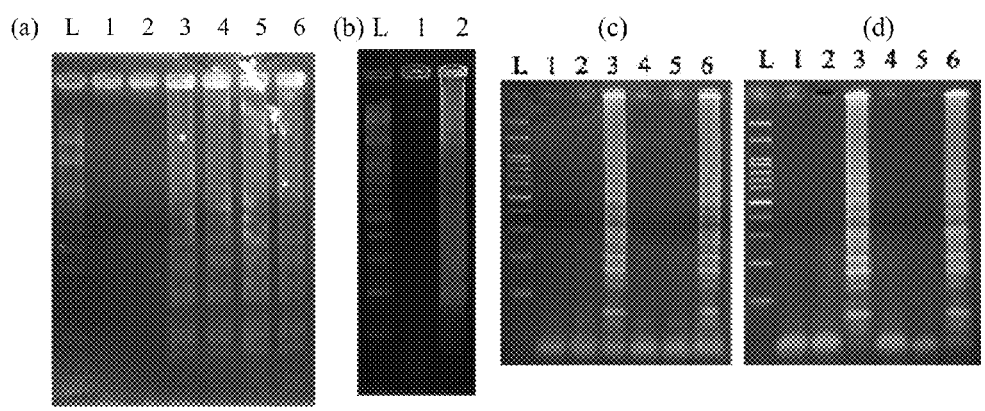
FIG. 5 shows that the method according to the invention can detect four pathogens of orchids by the LAMP or RT-LAMP; (a) Cymbidium mosaic virus, Lane L: 100 bp DNA ladder marker; Lane 1: DEPC-$H_2O$; Lane 2: RNA from the healthy tissue; Lane 3: hybridization at 67° C.; Lane 4: hybridization at 63° C.; Lane 5: hybridization at 60° C.; Lane 6: hybridization at 57° C.; (b) Odontoglossum ringspot virus, Lane L: 100 bp DNA ladder marker; Lane 1: RNA from the healthy tissue; Lane 2: test sample from the ORSV infected tissue; (c) Tomato spotted wilt virus, Lane L: 100 bp DNA ladder marker; Lane 1: dd$H_2O$ (microfluidic chip); Lane 2: RNA from the healthy tissue (microfluidic chip); Lane 3: test sample from the infected tissue (microfluidic chip); Lane 4: dd$H_2O$ (conventional); Lane 5: RNA from the healthy tissue (conventional); Lane 6: test sample from the infected tissue (conventional); (d) Capsicum chlorosis virus, Lane L: 100 bp DNA ladder marker; Lane 1: dd$H_2O$ (microfluidic chip); Lane 2: RNA from the healthy tissue (microfluidic chip); Lane 3: test sample from the infected tissue (microfluidic chip); Lane 4: dd$H_2O$ (conventional); Lane 5: RNA from the healthy tissue (conventional); Lane 6: test sample from the infected tissue (conventional).

FIG. 2 shows that the method according to the invention can detect three pathogens and an anti-virus protein of groupers by the LAMP. FIG. 3 shows that the method according to the invention can detect four pathogens of avians by the LAMP or RT-LAMP. FIG. 4 shows that the method according to the invention can detect four pathogens of plant seedlings by the LAMP. FIG. 5 shows that the method according to the invention can detect four pathogens of orchids by the LAMP or RT-LAMP. It shows that the method according to the invention has the high specificity.

While embodiments of the present invention have been illustrated and described, various modifications and improvements can be made by persons skilled in the art. The present invention is not limited to the particular forms as illustrated, and that all the modifications not departing from the spirit and scope of the present invention are within the scope as defined in the appended claims.

What is claimed is:

1. A method for detecting a pathogen in animals or plants, which comprises conducting loop-mediated isothermal amplification with at least one primer set and a nucleic acid in a test sample, and if at least one amplification is carried out, the test sample comprises the pathogen in animals or plants; wherein the primer set is selected from the group consisting of second to fourteenth primer sets, wherein:

the second primer set comprises primers comprising the sequences SEQ ID NOs. 6 to 9 or a sequence complementary thereof; the third primer set comprises primers comprising the sequences SEQ ID NOs. 11 to 14 or a sequence complementary thereof; the fourth primer set comprises primers comprising the sequences SEQ ID NOs. 16 to 19 or a sequence complementary thereof; the fifth primer set comprises primers comprising the sequences SEQ ID NOs. 21 to 24 or a sequence complementary thereof; the sixth primer set comprises primers comprising the sequences SEQ ID NOs. 26 to 29 or a sequence complementary thereof; the seventh primer set comprises primers comprising the sequences SEQ ID NOs. 31 to 34 or a sequence complementary thereof; the eighth primer set comprises primers comprising the sequences SEQ ID NOs. 36 to 39 or a sequence complementary thereof; the ninth primer set comprises primers comprising the sequences SEQ ID NOs. 41 to 44 or a sequence complementary thereof; the tenth primer set comprises primers comprising the sequences SEQ ID NOs. 46 to 49 or a sequence complementary thereof; the eleventh primer set comprises primers comprising the sequences SEQ ID NOs. 51 to 54 or a sequence complementary thereof; the twelfth primer set comprises primers comprising the sequences SEQ ID NOs. 56 to 59 or a sequence complementary thereof; the thirteenth primer set comprises primers comprising the sequences SEQ ID NOs. 61 to 64 or a sequence complementary thereof; and the fourteenth primer set comprises primers comprising the sequences SEQ ID NOs. 66 to 69 or a sequence complementary thereof.

2. The method according to claim 1, wherein the primer set comprises the second to fourteenth primer sets.

3. The method according to claim 1, wherein the third primer set further comprises a helper forward primer of SEQ ID NO. 75 and a helper reversed primer of SEQ ID NO. 76; the fifth primer set further comprises a helper forward primer of SEQ ID NO. 77 and a helper reversed primer of SEQ ID NO. 78; the sixth primer set further comprises a helper forward primer of SEQ ID NO. 79 and a helper reversed primer of SEQ ID NO. 80; the eleventh primer set further comprises a helper reversed primer of SEQ ID NO. 71; the twelfth primer set further comprises a helper reversed primer of SEQ ID NO. 72; the thirteenth primer set further comprises a helper reversed primer of SEQ ID NO. 73; and the fourteenth primer set further comprises a helper reversed primer of SEQ ID NO. 74.

4. The method according to claim 1, wherein:
- if the amplification is carried out with the nucleic acid in the test sample and the second primer set, the pathogen comprises *Vibrio* spp.;
- if the amplification is carried out with the nucleic acid in the test sample and the third primer set, the pathogen comprises Infectious Laryngotracheitis virus (ILTV);
- if the amplification is carried out with the nucleic acid in the test sample and the fourth primer set, the pathogen comprises newcastle disease virus (NDV);
- if the amplification is carried out with the nucleic acid in the test sample and the fifth primer set, the pathogen comprises avian reovirus (ARV);
- if the amplification is carried out with the nucleic acid in the test sample and the sixth primer set, the pathogen comprises avian influenza virus (AIV);
- if the amplification is carried out with the nucleic acid in the test sample and the seventh primer set, the pathogen comprises Cucumber mosaic virus (CMV);
- if the amplification is carried out with the nucleic acid in the test sample and the eighth primer set, the pathogen comprises Tobacco mosaic virus (TMV);
- if the amplification is carried out with the nucleic acid in the test sample and the ninth primer set, the pathogen comprises *Pectobacterium carotovorum* subsp. *Carotovorum*;
- if the amplification is carried out with the nucleic acid in the test sample and the tenth primer set, the pathogen comprises *Acidovorax avenae* subsp. *citrulli*;
- if the amplification is carried out with the nucleic acid in the test sample and the eleventh primer set, the pathogen comprises Cymbidium mosaic virus (CymMV);
- if the amplification is carried out with the nucleic acid in the test sample and the twelfth primer set, the pathogen comprises Odontoglossum ringspot virus (ORSV);
- if the amplification is carried out with the nucleic acid in the test sample and the thirteenth primer set, the pathogen comprises Tomato spotted wilt virus (TSWV); and
- if the amplification is carried out with the nucleic acid in the test sample and the fourteenth primer set, the pathogen comprises *Capsicum* chlorosis virus (CaCV).

5. The method according to claim 1, which further comprises conducting hybridization with at least one probe and the nucleic acid in the test sample, wherein the at least one probe comprises the sequence selected from the group consisting of SEQ ID NOs. 10, 15, 20, 25, 30, 35, 40, 45, 50, 55, 60, 65, and 70, or a sequence complementary thereof.

6. The method according to claim 5, wherein the at least one probe is linked to a magnetic bead.

7. The method according to claim 1, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

8. The method according to claim 2, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

9. The method according to claim 3, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

10. The method according to claim 5, which comprises the steps of:
    (a) purifying the nucleic acid in the test sample with a magnetic bead;
    (b) conducting loop-mediated isothermal amplification with the primer set and the nucleic acid in the step (a); and
    (c) detecting a product of the loop-mediated isothermal amplification.

11. The method according to claim 1, wherein the primer set further comprises a first primer set comprising primers comprising the sequences SEQ ID NOs. 1 to 4 or a sequence complementary thereof.

12. The method according to claim 11, which further comprises conducting hybridization with a probe of SEQ ID NOs. 5 and the nucleic acid in the test sample.

* * * * *

SEQUENCE LISTING

```
<160> NUMBER OF SEQ ID NOS: 80

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
ggtcatggtc aaggagcag                                              19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gctccatctt gaactgggtc                                             20

<210> SEQ ID NO 3
<211> LENGTH: 46
<212> TYPE: DNA
<213> ORGANISM: Artificial Sequence
<220> FEATURE:
<223> OTHER INFORMATION: primer

<400> SEQUENCE: 3
ggccagctgt atgaacgcct tcttttttca aacagctgga ggaacc                46

<210> SEQ ID NO 4
<211> LENGTH: 47
<212> TYPE: DNA
<213> ORGANISM: Artificial Sequence
<220> FEATURE:
<223> OTHER INFORMATION: primer

<400> SEQUENCE: 4
cagcgaaggc caagattgaa gcttttttctc agcatggatt cagcagt              47
```

```
<210> SEQ ID NO 5
<211> LENGTH: 31
<212> TYPE: DNA
<213> ORGANISM: Artificial Sequence
<220> FEATURE:
<223> OTHER INFORMATION: probe

<400> SEQUENCE: 5
tttttttttt cagctttcac tcaggatgcc a                              31

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tcattccaga ttggtgcgag                                           20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
cgccatcttt ggctaacaca                                           20

<210> SEQ ID NO 8
<211> LENGTH: 45
<212> TYPE: DNA
<213> ORGANISM: Artificial Sequence
<220> FEATURE:
<223> OTHER INFORMATION: primer

<400> SEQUENCE: 8
tgcaaggaac gattggccgc tttttcatta tggggcttac cagca               45

<210> SEQ ID NO 9
<211> LENGTH: 45
<212> TYPE: DNA
<213> ORGANISM: Artificial Sequence
<220> FEATURE:
<223> OTHER INFORMATION: primer

<400> SEQUENCE: 9
aaggacaagg attggggagt gcttttaac aagctcacct gcctg                45

<210> SEQ ID NO 10
<211> LENGTH: 31
<212> TYPE: DNA
<213> ORGANISM: Artificial Sequence
<220> FEATURE:
<223> OTHER INFORMATION: probe

<400> SEQUENCE: 10
tttttttttt atcagcaaac ggcaccaact c                              31

<210> SEQ ID NO 11
<211> LENGTH: 18
<212> TYPE: DNA
<213> ORGANISM: Artificial Sequence
<220> FEATURE:
<223> OTHER INFORMATION: primer
```

<400> SEQUENCE: 11
gcaaaatgtt cacgggga                                              18

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
tctactgcgt caattaagct                                            20

<210> SEQ ID NO 13
<211> LENGTH: 48
<212> TYPE: DNA
<213> ORGANISM: Artificial Sequence
<220> FEATURE:
<223> OTHER INFORMATION: primer

<400> SEQUENCE: 13
gctggtaagt aaaaaatgca caagtaaaac tgtactttca tttgtggt             48

<210> SEQ ID NO 14
<211> LENGTH: 41
<212> TYPE: DNA
<213> ORGANISM: Artificial Sequence
<220> FEATURE:
<223> OTHER INFORMATION: primer

<400> SEQUENCE: 14
cggaggcatg tgcactgaaa tcgtttggtt gtaagagaac t                    41

<210> SEQ ID NO 15
<211> LENGTH: 30
<212> TYPE: DNA
<213> ORGANISM: Artificial Sequence
<220> FEATURE:
<223> OTHER INFORMATION: probe

<400> SEQUENCE: 15
tttttttttt ggaaacggtc gactggacgt                                 30

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
tcaagggcct gtctcact                                              18

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
tctagggttc cactcccg                                              18

<210> SEQ ID NO 18
<211> LENGTH: 40
<212> TYPE: DNA
<213> ORGANISM: Artificial Sequence
<220> FEATURE:
<223> OTHER INFORMATION: primer

<400> SEQUENCE: 18
tggggtgcct gcactactga atgatggtca catgcgagaa                    40

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
ctgcaaagct gtagggttgt gctctctggc gctttcacgt                    40

<210> SEQ ID NO 20
<211> LENGTH: 30
<212> TYPE: DNA
<213> ORGANISM: Artificial Sequence
<220> FEATURE:
<223> OTHER INFORMATION: probe

<400> SEQUENCE: 20
tttttttttt gcaaatcgcc ccgcaatata                              30

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
acgcatatcc catcagacct                                          20

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
aggtgtcgat gccggtac                                            18

<210> SEQ ID NO 23
<211> LENGTH: 41
<212> TYPE: DNA
<213> ORGANISM: Artificial Sequence
<220> FEATURE:
<223> OTHER INFORMATION: primer

<400> SEQUENCE: 23
gtcgcagaat cgcgggtgaa tgttcctagt gcgggattcc a                  41

<210> SEQ ID NO 24
<211> LENGTH: 41
<212> TYPE: DNA
<213> ORGANISM: Artificial Sequence
<220> FEATURE:
<223> OTHER INFORMATION: primer

<400> SEQUENCE: 24
ggtgtactcg agctcacgtg tcgtcaagga acgaatgttc g    41

<210> SEQ ID NO 25
<211> LENGTH: 30
<212> TYPE: DNA
<213> ORGANISM: Artificial Sequence
<220> FEATURE:
<223> OTHER INFORMATION: probe

<400> SEQUENCE: 25
tttttttttt cggcgtggtt tcattagaca    30

<210> SEQ ID NO 26
<211> LENGTH: 20
<212> TYPE: DNA
<213> ORGANISM: Artificial Sequence
<220> FEATURE:
<223> OTHER INFORMATION: probe

<400> SEQUENCE: 26
tctaaccgag gtcgaaacgt    20

<210> SEQ ID NO 27
<211> LENGTH: 18
<212> TYPE: DNA
<213> ORGANISM: Artificial Sequence
<220> FEATURE:
<223> OTHER INFORMATION: primer

<400> SEQUENCE: 27
cgtctacgct gcagtcct    18

<210> SEQ ID NO 28
<211> LENGTH: 42
<212> TYPE: DNA
<213> ORGANISM: Artificial Sequence
<220> FEATURE:
<223> OTHER INFORMATION: primer

<400> SEQUENCE: 28
tcggtgttct tccctgcaaa gattctctct atcgtcccgt ca    42

<210> SEQ ID NO 29
<211> LENGTH: 42
<212> TYPE: DNA
<213> ORGANISM: Artificial Sequence
<220> FEATURE:
<223> OTHER INFORMATION: primer

<400> SEQUENCE: 29
tcgaggctct catggaatgg ctagcgtgaa cacaaaccct aa    42

<210> SEQ ID NO 30
<211> LENGTH: 30
<212> TYPE: DNA
<213> ORGANISM: Artificial Sequence
<220> FEATURE:
<223> OTHER INFORMATION: probe

<400> SEQUENCE: 30
tttttttttt ctactcagcc ggtgcacttg    30

```
<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
cgcgcattca aattcgagtt                                               20

<210> SEQ ID NO 32
<211> LENGTH: 19
<212> TYPE: DNA
<213> ORGANISM: Artificial Sequence
<220> FEATURE:
<223> OTHER INFORMATION: primer

<400> SEQUENCE: 32
ggcgtacttt cgcatgtcg                                                19

<210> SEQ ID NO 33
<211> LENGTH: 40
<212> TYPE: DNA
<213> ORGANISM: Artificial Sequence
<220> FEATURE:
<223> OTHER INFORMATION: primer

<400> SEQUENCE: 33
ggcggcaacg gataagtccg gattctaccg tgtgggtgac                         40

<210> SEQ ID NO 34
<211> LENGTH: 40
<212> TYPE: DNA
<213> ORGANISM: Artificial Sequence
<220> FEATURE:
<223> OTHER INFORMATION: primer

<400> SEQUENCE: 34
atcagtatgc cgcatccgga gatcgccgag agatcgtaca                         40

<210> SEQ ID NO 35
<211> LENGTH: 31
<212> TYPE: DNA
<213> ORGANISM: Artificial Sequence
<220> FEATURE:
<223> OTHER INFORMATION: probe

<400> SEQUENCE: 35
tttttttttt ccatgactca actcaaacgt c                                  31

<210> SEQ ID NO 36
<211> LENGTH: 18
<212> TYPE: DNA
<213> ORGANISM: Artificial Sequence
<220> FEATURE:
<223> OTHER INFORMATION: primer

<400> SEQUENCE: 36
aacgacagtt cagtgagg                                                 18

<210> SEQ ID NO 37
<211> LENGTH: 17
<212> TYPE: DNA
<213> ORGANISM: Artificial Sequence
<220> FEATURE:
<223> OTHER INFORMATION: primer
```

```
<400> SEQUENCE: 37
aacgtttcag cggttgt                                              17

<210> SEQ ID NO 38
<211> LENGTH: 43
<212> TYPE: DNA
<213> ORGANISM: Artificial Sequence
<220> FEATURE:
<223> OTHER INFORMATION: primer

<400> SEQUENCE: 38
ttgtacctgt acaccttaaa gtcactggaa accttcaccc caa                 43

<210> SEQ ID NO 39
<211> LENGTH: 44
<212> TYPE: DNA
<213> ORGANISM: Artificial Sequence
<220> FEATURE:
<223> OTHER INFORMATION: primer

<400> SEQUENCE: 39
tgcagtacta gatcctctaa tcacccgcct gattttcgac ttct                44

<210> SEQ ID NO 40
<211> LENGTH: 31
<212> TYPE: DNA
<213> ORGANISM: Artificial Sequence
<220> FEATURE:
<223> OTHER INFORMATION: probe

<400> SEQUENCE: 40
tttttttttt aagtctccga atcatctccg a                              31

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
cgtcaggtta tcaaagccca                                           20

<210> SEQ ID NO 42
<211> LENGTH: 19
<212> TYPE: DNA
<213> ORGANISM: Artificial Sequence
<220> FEATURE:
<223> OTHER INFORMATION: primer

<400> SEQUENCE: 42
tgccagtgaa catcgtgac                                            19

<210> SEQ ID NO 43
<211> LENGTH: 39
<212> TYPE: DNA
<213> ORGANISM: Artificial Sequence
<220> FEATURE:
<223> OTHER INFORMATION: primer

<400> SEQUENCE: 43
tgtttcggca ccagacggaa cggcagcaca ggaaatcct                      39
```

<210> SEQ ID NO 44
<211> LENGTH: 41
<212> TYPE: DNA
<213> ORGANISM: Artificial Sequence
<220> FEATURE:
<223> OTHER INFORMATION: primer

<400> SEQUENCE: 44
gcgttccatg atggatcgcg tatgcactgt tcaacgcaca a         41

<210> SEQ ID NO 45
<211> LENGTH: 31
<212> TYPE: DNA
<213> ORGANISM: Artificial Sequence
<220> FEATURE:
<223> OTHER INFORMATION: probe

<400> SEQUENCE: 45
tttttttttt ttcagtgctc tgttgcagag t              31

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
tcattacatt gcgcggaact                  20

<210> SEQ ID NO 47
<211> LENGTH: 19
<212> TYPE: DNA
<213> ORGANISM: Artificial Sequence
<220> FEATURE:
<223> OTHER INFORMATION: primer

<400> SEQUENCE: 47
cggtcgccag aaaaatcct                   19

<210> SEQ ID NO 48
<211> LENGTH: 41
<212> TYPE: DNA
<213> ORGANISM: Artificial Sequence
<220> FEATURE:
<223> OTHER INFORMATION: primer

<400> SEQUENCE: 48
ttccagcgat agggcgacat gattacctcg aagaccccgt t          41

<210> SEQ ID NO 49
<211> LENGTH: 36
<212> TYPE: DNA
<213> ORGANISM: Artificial Sequence
<220> FEATURE:
<223> OTHER INFORMATION: primer

<400> SEQUENCE: 49
gtttcggcac agggcgaccg caggcccaaa ccgtct              36

<210> SEQ ID NO 50
<211> LENGTH: 31
<212> TYPE: DNA
<213> ORGANISM: Artificial Sequence
<220> FEATURE:
<223> OTHER INFORMATION: probe

<400> SEQUENCE: 50
tttttttttt gatttcatcc agagagccaa c           31

<210> SEQ ID NO 51
<211> LENGTH: 19
<212> TYPE: DNA
<213> ORGANISM: Artificial Sequence
<220> FEATURE:
<223> OTHER INFORMATION: primer

<400> SEQUENCE: 51
tggtccagct attcaccgg           19

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
cggagtcagt gtcatcctca g           21

<210> SEQ ID NO 53
<211> LENGTH: 41
<212> TYPE: DNA
<213> ORGANISM: Artificial Sequence
<220> FEATURE:
<223> OTHER INFORMATION: primer

<400> SEQUENCE: 53
cgcacgtgta tggatggtct ctaagctctc gactggcaaa c           41

<210> SEQ ID NO 54
<211> LENGTH: 39
<212> TYPE: DNA
<213> ORGANISM: Artificial Sequence
<220> FEATURE:
<223> OTHER INFORMATION: primer

<400> SEQUENCE: 54
cgcttcgcat gtgcagagac ccgtcaggga gctgtctga           39

<210> SEQ ID NO 55
<211> LENGTH: 30
<212> TYPE: DNA
<213> ORGANISM: Artificial Sequence
<220> FEATURE:
<223> OTHER INFORMATION: probe

<400> SEQUENCE: 55
tttttttttt tccacagggt caaaaaggtc           30

<210> SEQ ID NO 56
<211> LENGTH: 19
<212> TYPE: DNA
<213> ORGANISM: Artificial Sequence
<220> FEATURE:
<223> OTHER INFORMATION: primer

<400> SEQUENCE: 56
atactgccga acttgtagt           19

```
<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
actcatcttg aggactgaga                                                  20

<210> SEQ ID NO 58
<211> LENGTH: 43
<212> TYPE: DNA
<213> ORGANISM: Artificial Sequence
<220> FEATURE:
<223> OTHER INFORMATION: primer

<400> SEQUENCE: 58
ggcatctgaa gtcatcggtg tagggatgct tacattattg acg                        43

<210> SEQ ID NO 59
<211> LENGTH: 42
<212> TYPE: DNA
<213> ORGANISM: Artificial Sequence
<220> FEATURE:
<223> OTHER INFORMATION: primer

<400> SEQUENCE: 59
tcacaggtgg atggctaagc tgtattgatc aatagcgggt aa                         42

<210> SEQ ID NO 60
<211> LENGTH: 29
<212> TYPE: DNA
<213> ORGANISM: Artificial Sequence
<220> FEATURE:
<223> OTHER INFORMATION: probe

<400> SEQUENCE: 60
tttttttttt cgaactgctg ctgaacgtc                                        29

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
catgaccttc agaaggct                                                    18

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
agacaacact gatcatctca                                                  20

<210> SEQ ID NO 63
<211> LENGTH: 43
<212> TYPE: DNA
<213> ORGANISM: Artificial Sequence
<220> FEATURE:
<223> OTHER INFORMATION: primer
```

<400> SEQUENCE: 63
ggtgggaagc aatcttagat ttgatcttga tcagggtcag gct         43

<210> SEQ ID NO 64
<211> LENGTH: 45
<212> TYPE: DNA
<213> ORGANISM: Artificial Sequence
<220> FEATURE:
<223> OTHER INFORMATION: primer

<400> SEQUENCE: 64
atggattacc tcttgatgat gcaactgaag caataagagg taagc       45

<210> SEQ ID NO 65
<211> LENGTH: 29
<212> TYPE: DNA
<213> ORGANISM: Artificial Sequence
<220> FEATURE:
<223> OTHER INFORMATION: probe

<400> SEQUENCE: 65
tttttttttt gctttgcttt tcagcacgg                         29

<210> SEQ ID NO 66
<211> LENGTH: 23
<212> TYPE: DNA
<213> ORGANISM: Artificial Sequence
<220> FEATURE:
<223> OTHER INFORMATION: primer

<400> SEQUENCE: 66
gcacaagaat gatatacaga tga                               23

<210> SEQ ID NO 67
<211> LENGTH: 25
<212> TYPE: DNA
<213> ORGANISM: Artificial Sequence
<220> FEATURE:
<223> OTHER INFORMATION: primer

<400> SEQUENCE: 67
gagtgtataa tgatgtatgt aaagc                             25

<210> SEQ ID NO 68
<211> LENGTH: 44
<212> TYPE: DNA
<213> ORGANISM: Artificial Sequence
<220> FEATURE:
<223> OTHER INFORMATION: primer

<400> SEQUENCE: 68
tggaacttca ctatctgtct tgacattcaa gttcccttga agcc        44

<210> SEQ ID NO 69
<211> LENGTH: 46
<212> TYPE: DNA
<213> ORGANISM: Artificial Sequence
<220> FEATURE:
<223> OTHER INFORMATION: primer

<400> SEQUENCE: 69
gatccgtatt ctgtttgtcc tcttttaaga gagtttgcat tcctac      46

<210> SEQ ID NO 70
<211> LENGTH: 36
<212> TYPE: DNA
<213> ORGANISM: Artificial Sequence
<220> FEATURE:
<223> OTHER INFORMATION: probe

<400> SEQUENCE: 70
tttttttttt gccatatctg actttcatga atgttc                           36

<210> SEQ ID NO 71
<211> LENGTH: 24
<212> TYPE: DNA
<213> ORGANISM: Artificial Sequence
<220> FEATURE:
<223> OTHER INFORMATION: primer

<400> SEQUENCE: 71
taccatgcga tgaatatgat cgtg                                         24

<210> SEQ ID NO 72
<211> LENGTH: 24
<212> TYPE: DNA
<213> ORGANISM: Artificial Sequence
<220> FEATURE:
<223> OTHER INFORMATION: primer

<400> SEQUENCE: 72
attggtcaat tagctgattt tgac                                         24

<210> SEQ ID NO 73
<211> LENGTH: 22
<212> TYPE: DNA
<213> ORGANISM: Artificial Sequence
<220> FEATURE:
<223> OTHER INFORMATION: primer

<400> SEQUENCE: 73
ggcttgccat aatgctggga gg                                           22

<210> SEQ ID NO 74
<211> LENGTH: 23
<212> TYPE: DNA
<213> ORGANISM: Artificial Sequence
<220> FEATURE:
<223> OTHER INFORMATION: primer

<400> SEQUENCE: 74
cacgttccca gtatcaatga act                                          23

<210> SEQ ID NO 75
<211> LENGTH: 21
<212> TYPE: DNA
<213> ORGANISM: Artificial Sequence
<220> FEATURE:
<223> OTHER INFORMATION: primer

<400> SEQUENCE: 75
aataccgtcg cgagttttg a                                             21

<210> SEQ ID NO 76
<211> LENGTH: 21
<212> TYPE: DNA
<213> ORGANISM: Artificial Sequence
<220> FEATURE:
<223> OTHER INFORMATION: primer

```
<400> SEQUENCE: 76
tgtttagagt ttgccgagac g                                             21

<210> SEQ ID NO 77
<211> LENGTH: 19
<212> TYPE: DNA
<213> ORGANISM: Artificial Sequence
<220> FEATURE:
<223> OTHER INFORMATION: primer

<400> SEQUENCE: 77
tacgtccaca gggaacgac                                                19

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
ttactttccc aaccggaggt                                               20

<210> SEQ ID NO 79
<211> LENGTH: 19
<212> TYPE: DNA
<213> ORGANISM: Artificial Sequence
<220> FEATURE:
<223> OTHER INFORMATION: primer

<400> SEQUENCE: 79
atctcggctt tgagggggc                                                19

<210> SEQ ID NO 80
<211> LENGTH: 25
<212> TYPE: DNA
<213> ORGANISM: Artificial Sequence
<220> FEATURE:
<223> OTHER INFORMATION: primer

<400> SEQUENCE: 80
aagaccaatc ctgtcacctc tgact                                         25
```